US012661106B2

(12) United States Patent
Massey

(10) Patent No.: US 12,661,106 B2
(45) Date of Patent: Jun. 23, 2026

(54) EXPANDABLE SYNTHETIC SLEEVE TO AFFIX TISSUE

(71) Applicant: Patrick Massey, Shreveport, LA (US)

(72) Inventor: Patrick Massey, Shreveport, LA (US)

( * ) Notice: Subject to any disclaimer, the term of this patent is extended or adjusted under 35 U.S.C. 154(b) by 299 days.

(21) Appl. No.: 18/342,049

(22) Filed: Jun. 27, 2023

(65) Prior Publication Data

US 2024/0252161 A1      Aug. 1, 2024

Related U.S. Application Data

(60) Provisional application No. 63/442,312, filed on Jan. 31, 2023.

(51) Int. Cl.
A61B 17/04          (2006.01)

(52) U.S. Cl.
CPC .. A61B 17/0401 (2013.01); *A61B 2017/0414* (2013.01); *A61B 2017/0458* (2013.01)

(58) Field of Classification Search
CPC ........ A61B 17/0401; A61B 2017/0414; A61B 2017/042; A61B 2017/0445; A61B 2017/0446; A61B 2017/0448; A61B 2017/0458; A61B 2017/0459
See application file for complete search history.

(56) References Cited

U.S. PATENT DOCUMENTS 10,070,856 B1 * 9/2018 Black ................. A61B 17/0401
11,812,941 B2 * 11/2023 Rodriguez ......... A61B 17/0401

| | | | |
|---|---|---|---|
| 2012/0239086 A1 | 9/2012 | Reznik et al. | |
| 2013/0261665 A1 | 10/2013 | Yeung et al. | |
| 2016/0128684 A1 | 5/2016 | Stone et al. | |
| 2016/0157980 A1 | 6/2016 | Poucher et al. | |
| 2016/0296222 A1 | 10/2016 | Sengun | |
| 2019/0247039 A1 * | 8/2019 | Gregoire | ............ A61B 17/0401 |
| 2022/0240918 A1 * | 8/2022 | Qi | ....................... A61B 17/0401 |
| 2023/0133232 A1 * | 5/2023 | Patel | .................. A61B 17/0401 |
| | | | 606/232 |
| 2024/0415505 A1 * | 12/2024 | Housman | ........... A61B 17/0401 |

OTHER PUBLICATIONS

International Preliminary Report on Patentability issued on Aug. 14, 2025, in corresponding International Application No. PCT/US2024/012568, 9 pages.
International Search Report and Written Opinion issued on May 6, 2024, in corresponding International Application No. PCT/US2024/012568, 10 pages.

* cited by examiner

*Primary Examiner* — Dianne Dornbusch
(74) *Attorney, Agent, or Firm* — Maier & Maier, PLLC

(57) ABSTRACT

Implants and instrumentations for fixation of tissue to bone may be provided. An expandable locking suture sleeve may provide knotless fixation of sutures and soft tissue. The locking suture sleeve may have an internal mechanism to lock extra-sleeve or tissue repair sutures through a locking loop. An insertion device may further be provided. The insertion device may have a cannulated inner wire to hold the locking sleeve sutures. The insertion device may have a driver with a receptable screw that can be advanced down the inner wire. The receptacle screw may be buried into the patient's bone to compress the suture sleeve and further lock the sutures in place. A back handle may be threaded into the screw driver in order to control the advancement of the screw.

5 Claims, 25 Drawing Sheets

100

202

204

206

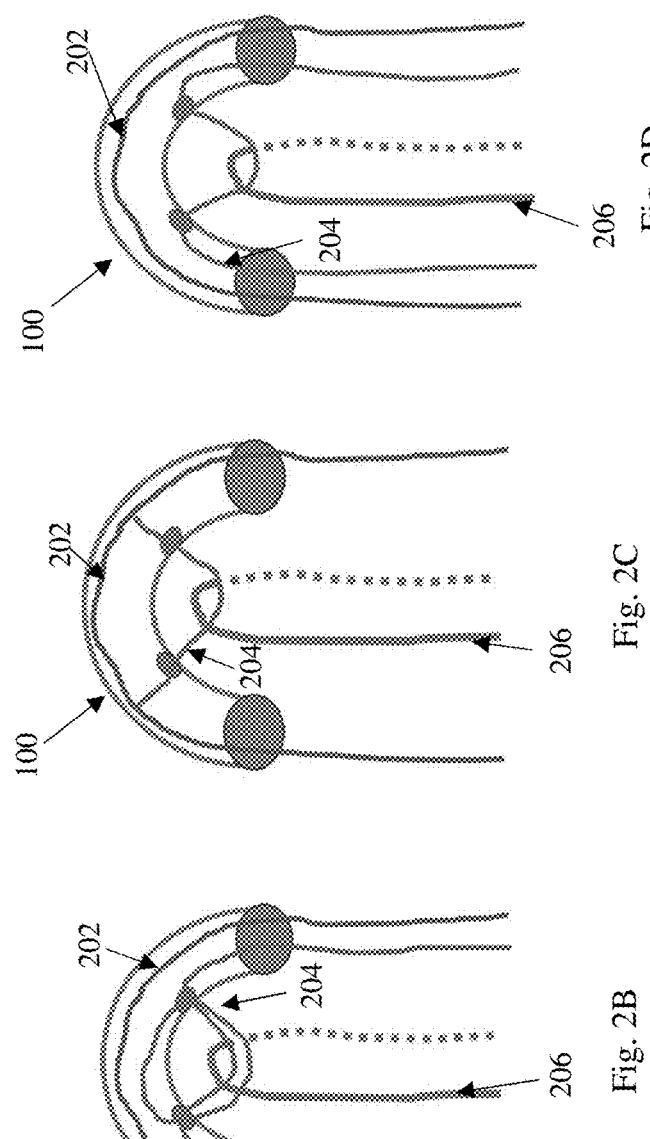
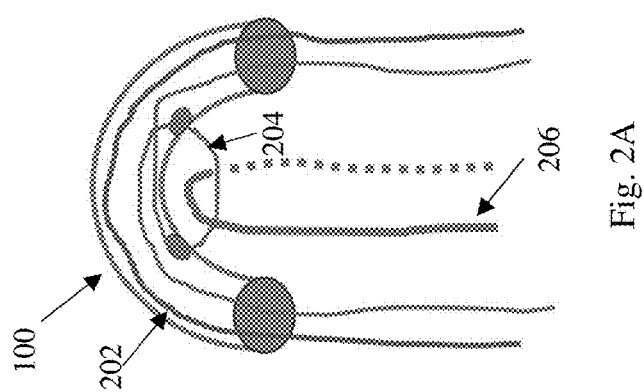

300

302

304

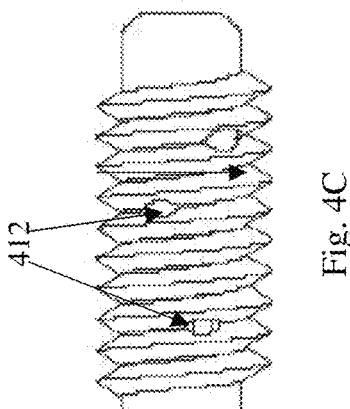
Fig. 4C
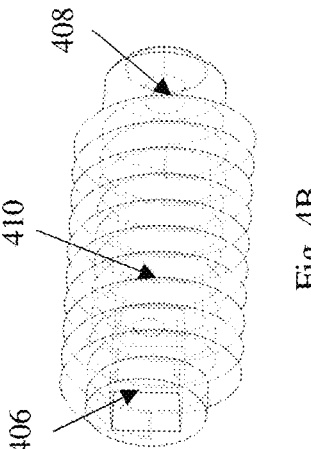
Fig. 4B
400
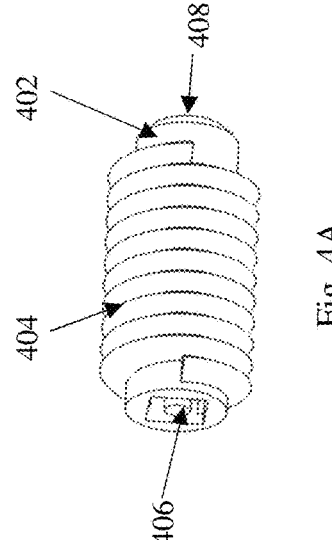
Fig. 4A

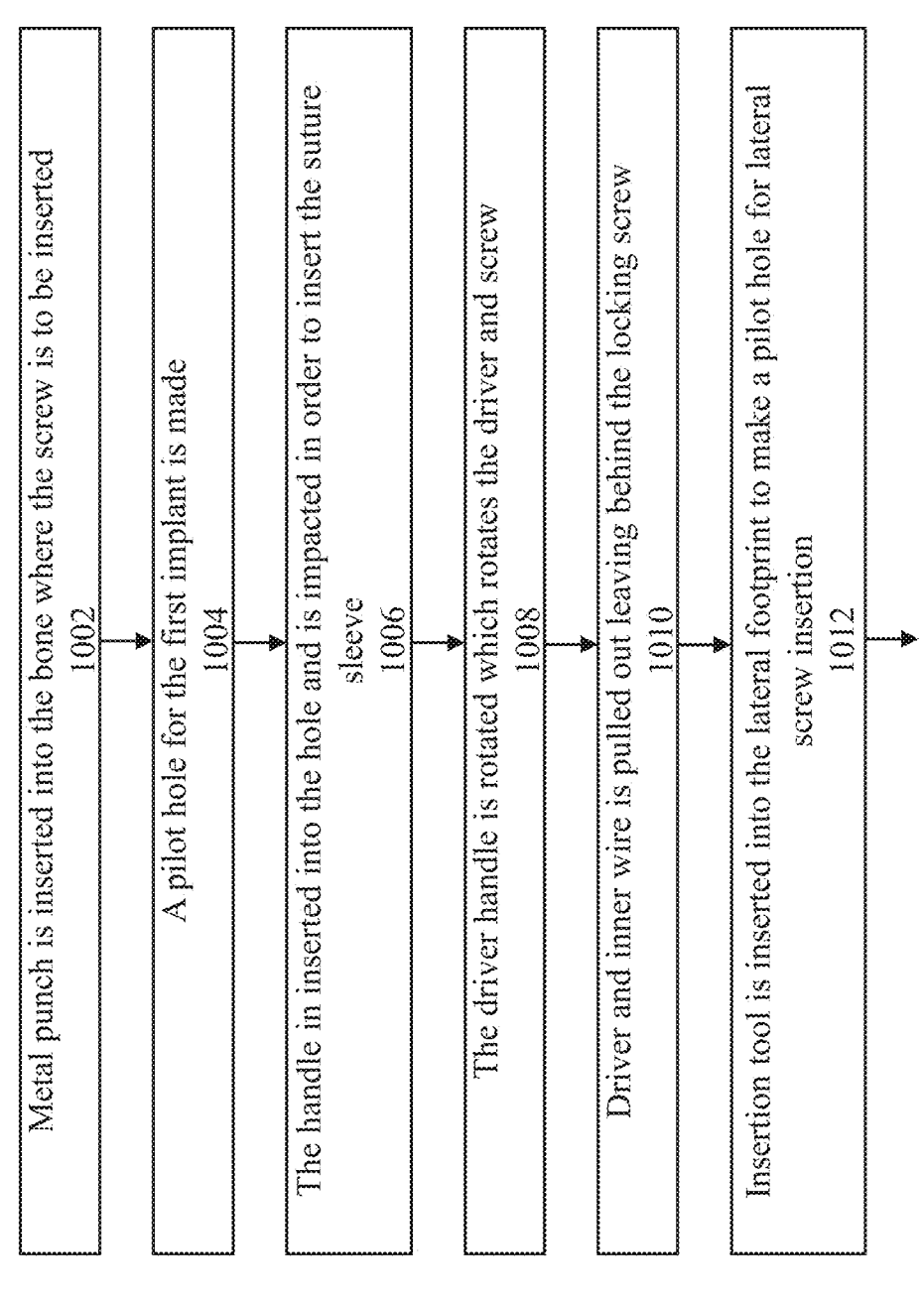

Metal punch is inserted into the bone where the screw is to be inserted
1002

A pilot hole for the first implant is made
1004

The handle in inserted into the hole and is impacted in order to insert the suture sleeve
1006

The driver handle is rotated which rotates the driver and screw
1008

Driver and inner wire is pulled out leaving behind the locking screw
1010

Insertion tool is inserted into the lateral footprint to make a pilot hole for lateral screw insertion
1012

Figure 10B:
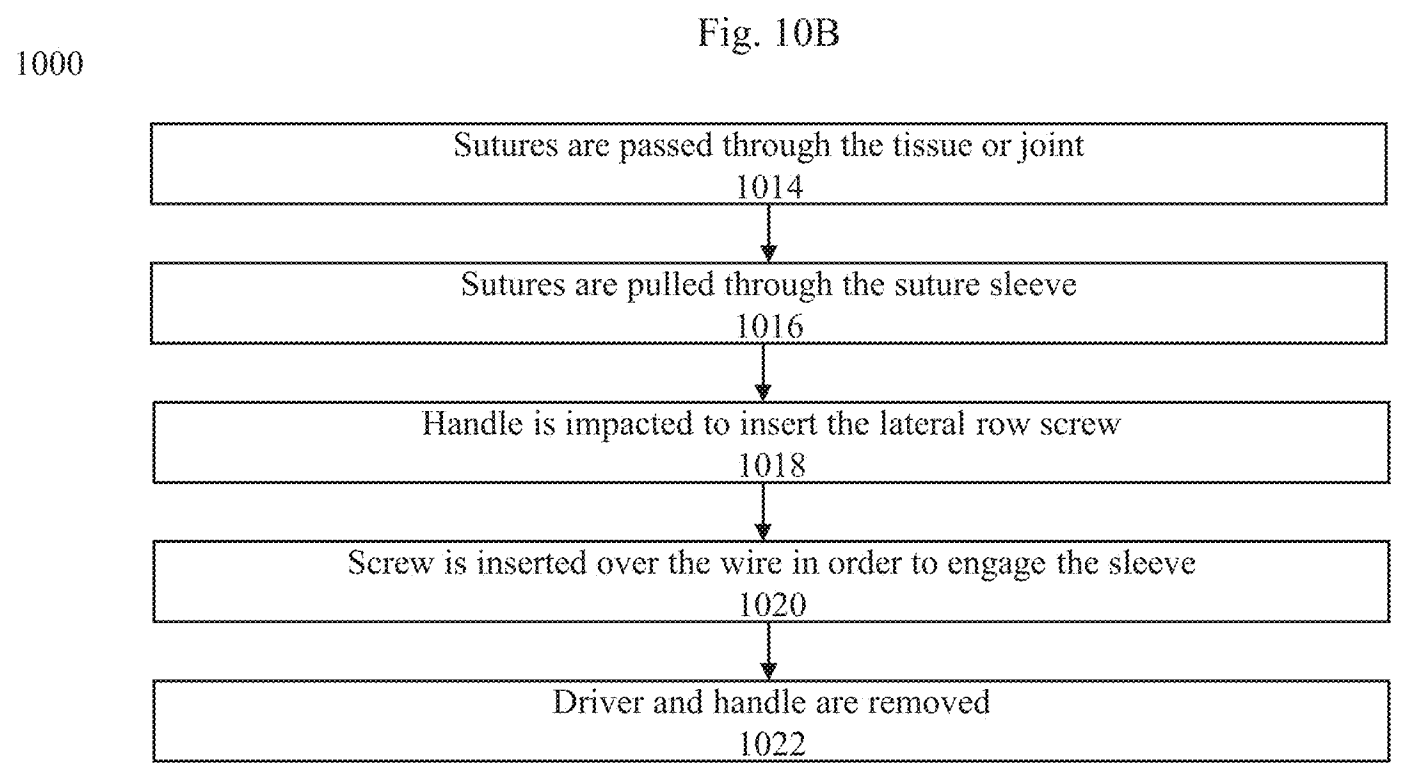

Sutures are passed through the tissue or joint
1014

Sutures are pulled through the suture sleeve
1016

Handle is impacted to insert the lateral row screw
1018

Screw is inserted over the wire in order to engage the sleeve
1020

Driver and handle are removed
1022

EXPANDABLE SYNTHETIC SLEEVE TO AFFIX TISSUE

BACKGROUND

When musculoskeletal injuries occur acutely or over time, a tendon or ligament can pull away from bone. Surgery can be performed with the goal to reattach the tendon or ligament back to its original insertion point on the bone. In most existing cases a screw is used to attach the tendon or ligament to the appropriate bone. However, locations for tissue fixation such as the greater tuberosity can have osteoporotic bone or poor bone quality. This can cause loss of fixation of suture anchors used to repair the tissue.

SUMMARY

One or more implants and instrumentations for fixation of tissue to bone may be provided. In one or more embodiments an expandable locking suture sleeve may provide knotless fixation of sutures and soft tissue. The locking suture sleeve may have an internal mechanism to lock extra-sleeve or tissue repair sutures through a locking loop. An insertion device may further be provided. The insertion device may have a cannulated inner wire to hold the locking sleeve sutures. The insertion device may have a driver with a receptable screw that can be advanced down the inner wire. The receptacle screw may be buried into the patient's bone to compress the suture sleeve and further lock the sutures in place. A back handle may be threaded into the screw driver in order to control the advancement of the screw.

In some embodiments a double diameter screw may be utilized to create a larger hole for placement of a tendon or tissue. In other embodiments a triple diameter reamer or drill may be used to make 3 size holes for placement of the sleeve, tissue, and/or screws.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 2A shows an exemplary embodiment of suture sleeves passing through the suture sleeve.

FIG. 2B shows another exemplary embodiment of suture sleeves passing through the suture sleeve.

FIG. 2C shows another exemplary embodiment of suture sleeves passing through the suture sleeve.

FIG. 2D shows another exemplary embodiment of suture sleeves passing through the suture sleeve.

FIG. 4A shows exemplary screw.

FIG. 4B shows an internal view of an exemplary screw.

FIG. 4C shows another exemplary screw.

FIG. 5 shows the exemplary back handle for a driver.

FIG. 9 shows an exemplary suture sleeve with suture strands passing through.

FIG. 10A shows an exemplary method for affixing tissue to bone utilizing a suture sleeve.

FIG. 10B continues showing the exemplary method for affixing tissue to bone utilizing a suture sleeve.

FIG. 22 shows an exemplary double diameter screw.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
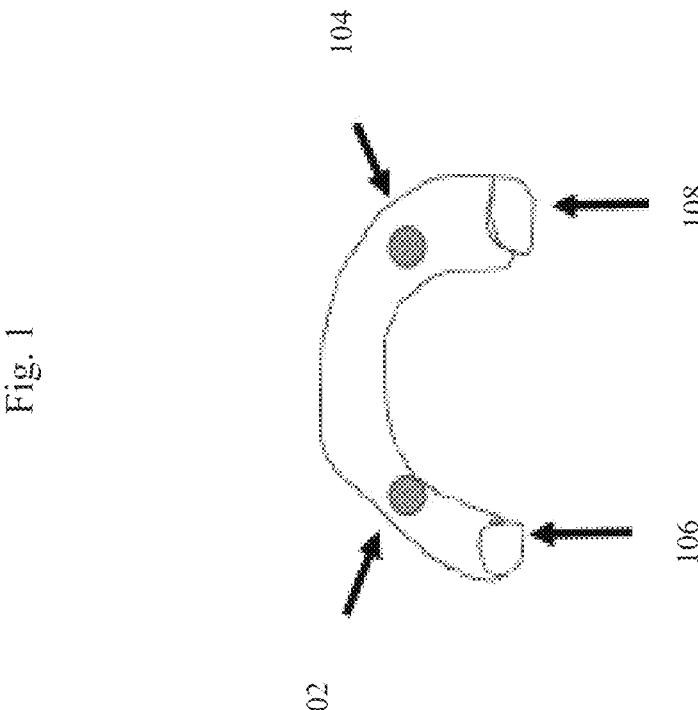
FIG. 1 shows an exemplary suture sleeve.

FIG. 1 may show an exemplary suture sleeve 100. The sleeve 100 may be may of a synthetic material, for example polyester or polyethylene. The sleeve 100 may be a cylindrical shape, and may have a first hole 102 and a second hole 104 which may be punctured into the side of the sleeve 100. In some embodiments the first hole 102 and the second hole 104 may be staggered on each side of the sleeve, which may prevent an area of weakness in the screw. In other embodiments the holes may be on opposite sides of the sleeve 100. The sleeve 100 may further have a first opening 106 at one end of the sleeve 100 and a second opening 108 at the opposite end of the sleeve 100.

Referring to FIGS. 2A-2D generally, one or more sutures including, for example, a core sliding suture 202 and/or a locking suture 204 may be passed through the sleeve 100 in a variety of configurations. In some embodiments there may further be an extra-sleeve suture 206. The extra-sleeve suture 206 may be utilized for the fixation of tissue, while the locking suture 204 may be utilized in order to lock the sleeve 100. In an embodiment the locking suture 204 may be tensioned, which may lock the extra-sleeve suture 206 or tissue suture.

In exemplary FIG. 2A the locking suture 204 may be passed through the first opening 106, through the sleeve 100, out the second hole 104, looped back through the first hole 102, through the elbow, and finally out the second opening 108. It may be understood that the extra-sleeve 206 or tissue suture may be passed through the exterior looped portion of the locking suture. In Exemplary FIG. 2B the locking suture 204 may be passed through the first opening 106, through the first hole 102 and the second hole 104 backwards through the sleeve 100, back out the first hole 102 and second hole 104, and finally out the second opening 108. In exemplary FIG. 2C the core suture 202 may be passed through the first opening 106, through the elbow and out the second opening 108. There may then be a locking suture 204 or connection suture that goes from the first hole 102 to the second hole 104, and in some embodiments this may be part of the core suture. In exemplary FIG. 2D the core suture 202 may be passed through the first opening 106, through the sleeve 100 and out the second opening 108. The locking suture 204 may also pass through opening 106, out hole 102 and back in through hole 104, before exiting through the second opening 108. In some embodiments a single suture may be used, for example the configurations shown in FIGS. 2A and 2B. In other embodiments multiple sutures may be used, either tied end to end or used side by side, for example in the configurations shown in FIGS. 2C and 2D.

In an exemplary embodiment the suture sleeve may be inserted folded in half. When pulling on the core suture 202 the sleeve may expand and engage into the surrounding tissue. When the locking suture 204 is tensioned the sleeve may "lock" the extra-sleeve suture 206 in place, which may be at a constant tension. The extra-sleeve suture 206 may first be passed through tissue or bone, and therefore after being locked may securely hold the tissue in place.

Figure 3:
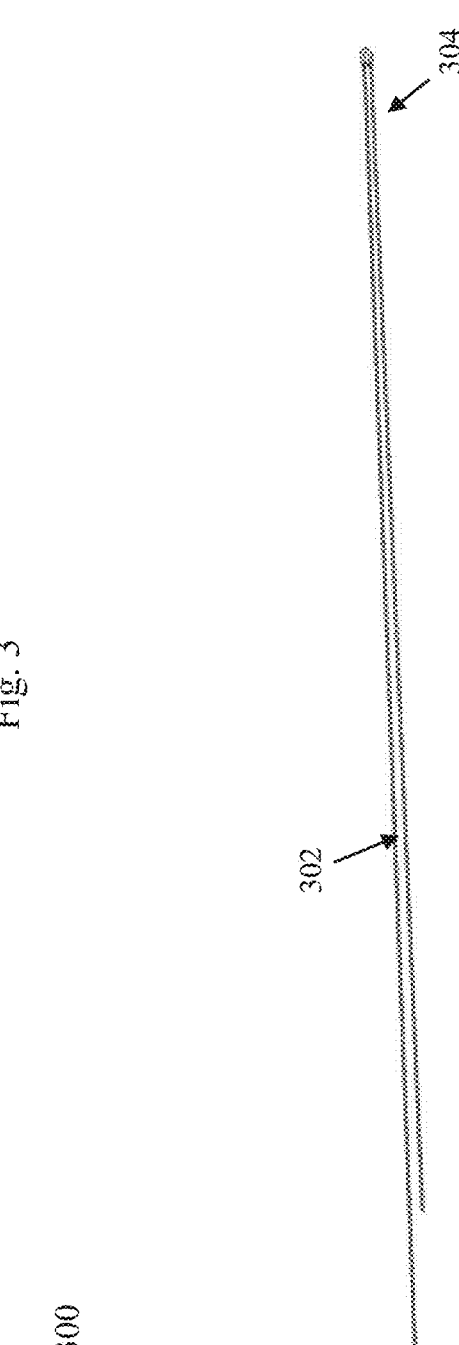
FIG. 3 shows an exemplary suture strand with suture sleeve.

Exemplary FIG. 3 shows a suture strand with suture sleeve 300. There may be a plurality of suture strands 302, for example there may be 1, 2, or 3 sets of sutures which may result in 2, 4, or 6 strands respectively. The suture strands 302 may pass out of the suture sleeve 304, which may lock an extra-sleeve suture once tension is pulled on the strands 302.

FIGS. 4A-4C show exemplary screws 400 that may be used in conjunction with a suture and/or suture sleeve in order to affix tissue to bone. The screw 400 may be, for example, a titanium alloy, titanium, plastic, poly ether ether ketone (PEEK), and/or other metal screw. In some embodiments the screw 400 may be absorbable, and may be made of, for example, L-lactic acid, β-tricalcium, phosphate, titanium, poly ether ether ketone (PEEK), titanium alloy, stainless steel, and/or cobalt chromium. It may be understood that in some embodiments the screw 400 may be made of a combination of materials.

The screw 400 may have a distal end 402, which may lock the suture sleeve in place when affixing tissue to the patient's body. The distal end 402 may have a variety of possible shapes, including, but not limited to, concave, convex, beveled, conical, or indented cross shape. The screw 400 may further have an exterior threaded cylinder 404, and an inner cannulated threading 410 that may act as track advancement when used by, for example, a driver. In some embodiments the inner threading may only be maintained for a portion of the screw length, and the distal end 402 may lack internal threading and be denser than the rest of the screw. The screw 400 may further have a back handle recess 406 which may interface with, for example, the driver. The back handle recess 406 may be, for example, square shaped, star shaped, hexagon shaped, or any other shape that corresponds to the driver. The screw 400 may further contain a suture entry hole 408 which may allow a wire, shaft, and/or suture to run through the screw 400. In some embodiments the screw 400 may have a plurality of vent holes 412, which may allow bone marrow or other fluids and cells to pass through the inside of the screw 400 from outside the screw 400 and vice versa.

Figure 5:
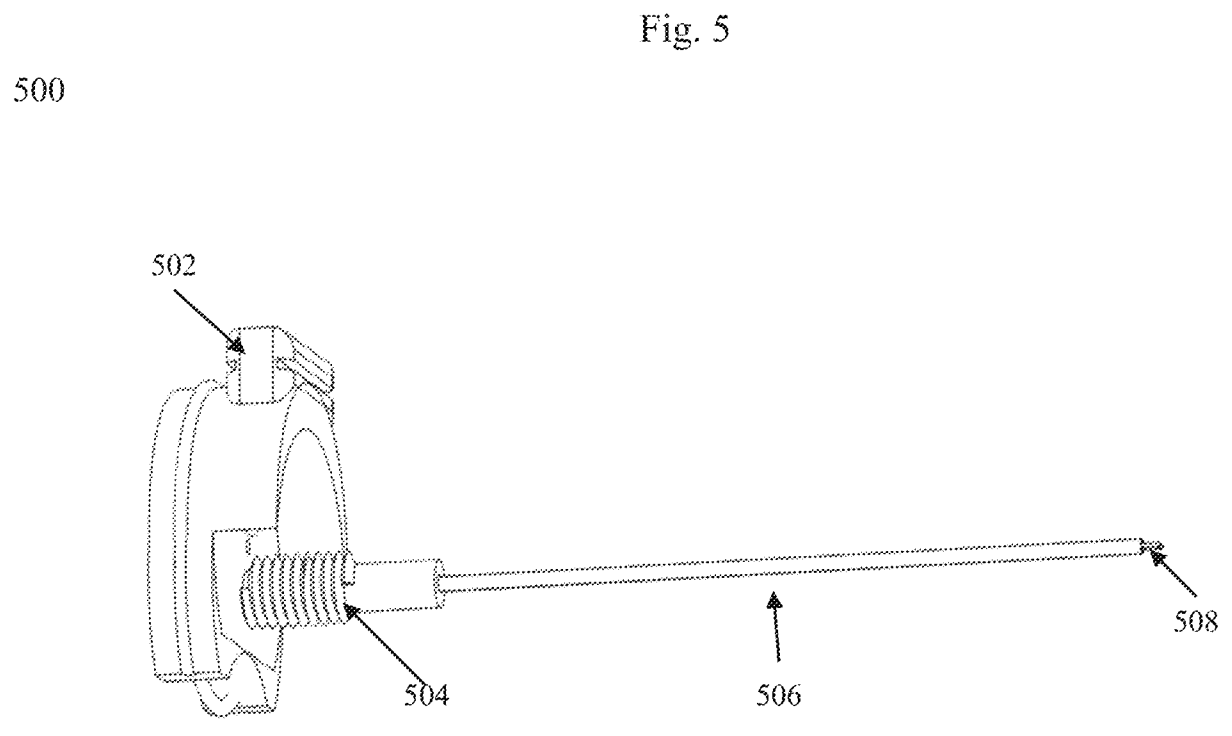

Referring generally to FIGS. 5-9, a driver for utilizing the exemplary suture stand with suture sleeve and screw may now be described. In some embodiments the driver may be composed of a plurality of sub-pieces, for example a back handle 500, FIG. 5 shows the exemplary back handle 500 for a driver for affixing tissue to bone. The back handle may have cleats 502 or another structure to wrap or lock sutures to the driver 500. The back handle 500 may further be threaded 504. In some embodiments the back handle 500 may have an inner wire and/or cannulated tube for the screw to advance down. In some embodiments the inner wire may have two or more prongs that hold the expandable suture sleeve. The cannulated tube may have a double barrel 506 with cannulated holes that hold one or more pairs of sutures from the suture sleeve. The end of the back handle 500 may have a semi-circular device 508 or other means for holding the suture sleeve in place during insertion into the bone.

Figure 6:
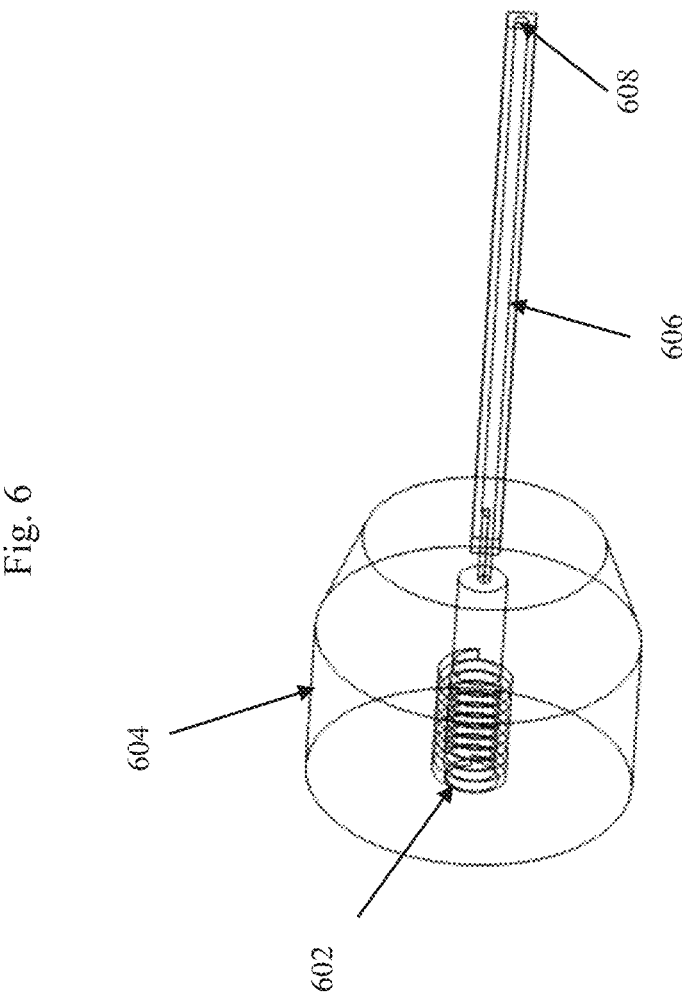
FIG. 6 shows an exemplary driver handle.

FIG. 6 shows an exemplary driver handle 600 which may be combined with the back handle 500 in order to drive the screw. The driver handle 600 may thread onto the back handle 500 through threading 602. the driver handle 600 may have a handle 604 that can be easily grasped by a physician or medical professional using the device. The screw may screw onto the end of the driver handle 604, the screw connection may be, for example but not limited to, square shaped, star shaped, hexagon shaped, or octagon shaped. The driver handle 600 may further have a screw insertion tube 606, which may hold the sutures traveling from the screw. A suture sleeve 608 may be held at the tip of the driver handle 600.

Figure 7:
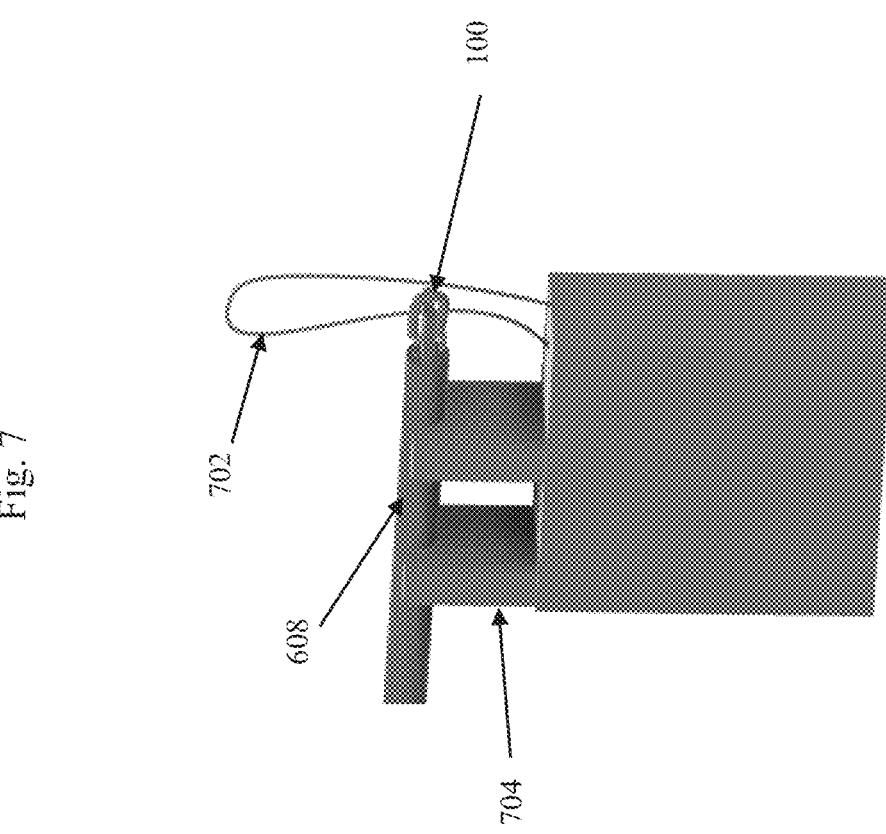
FIG. 7 shows an exemplary clip with wire loop.

FIG. 7 shows an exemplary clip with wire loop 700, which may be used to attach the screw insertion tube 606 to the suture sleeve and sutures. The clip 700 may include a wire loop 702, which may pass through the suture sleeve sutures. The clip 700 may attach to the driver through one or more connectors 704. The clip 700 may be used to pass extra-sleeve sutures through the locking sleeve.

Figure 8:
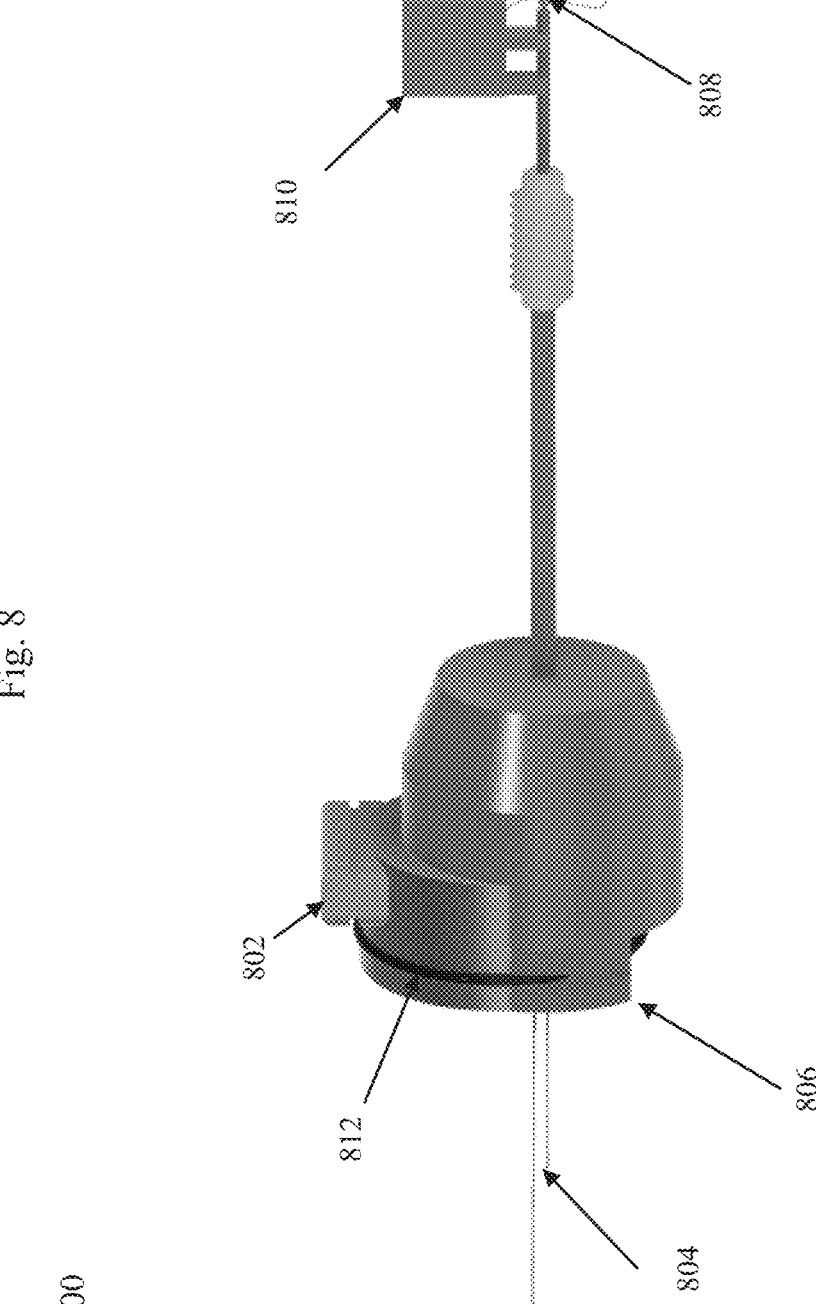
FIG. 8 shows an exemplary driver.

FIG. 8 shows an exemplary driver 800, which may be a combination of the driver back handle 500 and the driver handle 600. The driver 800 may have cleats for wrapping or locking sutures 804. The driver 800 may have a handle portion 806 that is reinforced to withstand impaction by a hammer. The suture sleeve may be held at the end of the driver through a pronged semicircular device 808, which may be secured via a clip 810. The sutures 804 may be held through double barrel cannulations in the driver 800. Finally, the driver 800 may have a back ring 812, which may be made of, for example, rubber, and may wrap around the driver 800 to hold the suture 804 in place.

Figure 9:
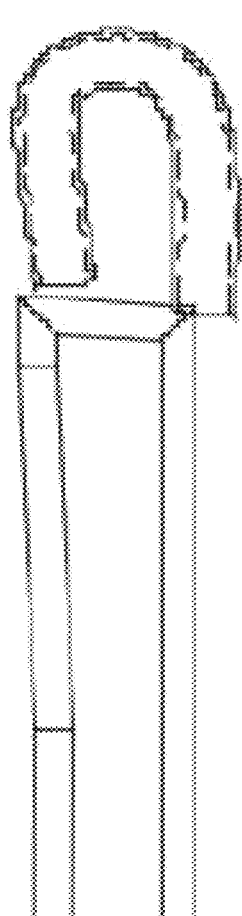

FIG. 9 shows an exemplary suture sleeve with suture strands passing through 900.

FIG. 10 shows an exemplary method for affixing tissue to bone utilizing a suture sleeve. In a first step 1002 a metal punch may be inserted into the patient's bone where a first screw is to be implanted. In some embodiments the screw may need to be inserted into muscle or other tissue, for example the patient's rotator cuff, calcaneous, patella tendon, quardriceps tendon, hamstring tendon, elbow ligaments, knee ligaments, etc. In a next step 1004 the metal punch may be removed leaving a pilot hole in the bone or tissue. In a next step 1006 the handle may be inserted into the pilot hole, and may be impacted with, for example, a hammer in order to insert the suture sleeve into the pilot hole. The impaction may advance the screw down the handle until the tip is inserted into the pilot hole.

In a next step 1008, the driver handle may be rotated in order to rotate the driver and the screw. The screw may advance down an inner wire into the bone. During advancement of the driver, the driver may rotate around the threaded track of the back handle. The medial fixation device may now be deployed. In a next step 1010, the driver and inner wire may be pulled out, and the sutures may be pulled out of the cannulated wire, leaving behind the screw for the medial row. In a next step 1012 an insertion tool, for example an awl, punch, or tap, may be inserted into the footprint lateral footprint to make a pilot hole for the lateral screw insertion. In a next step 1014 the sutures may be passed through the tissue or muscle, and in some embodiments may be passed through another suture sleeve with a wire loop. In a next step the 1016 the sutures from the first anchor may be pulled through the suture sleeve. In a next step 1018 the back handle may be impacted to insert the lateral row screw into the pilot hole in the lateral footprint. In a next step 1020 the suture coming from the medial anchor may be tensioned and locked to the handle, for example on the handle cleat. The suture sleeve may then be locked by pulling on the sutures and inserting the screw over the wire to engage the sleeve fully.

Figure 11:
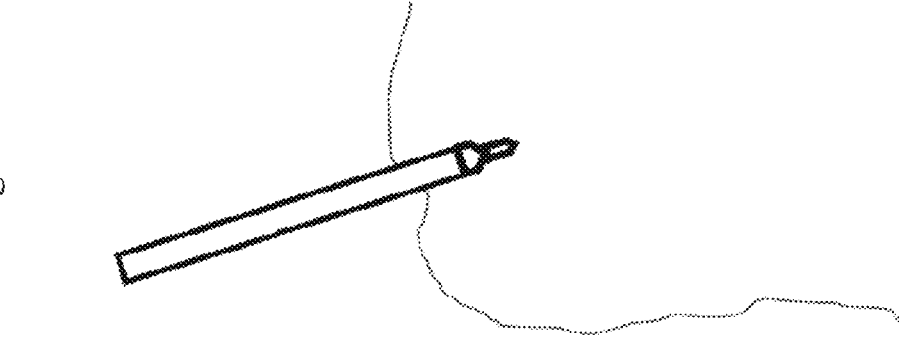
FIG. 11 shows step 1002 of the exemplary method shown in FIG. 10.
Figure 12:
FIG. 12 shows step 1004 of the exemplary method shown in FIG. 10.
Figure 13:
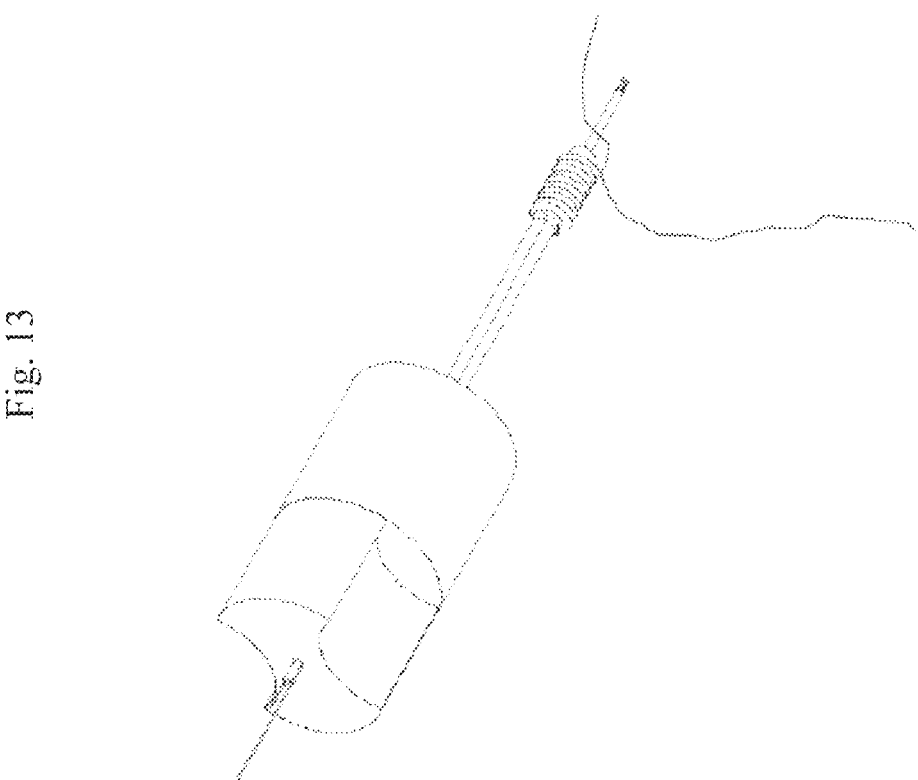
FIG. 13 shows step 1006 of the exemplary method shown in FIG. 10.
Figure 14:
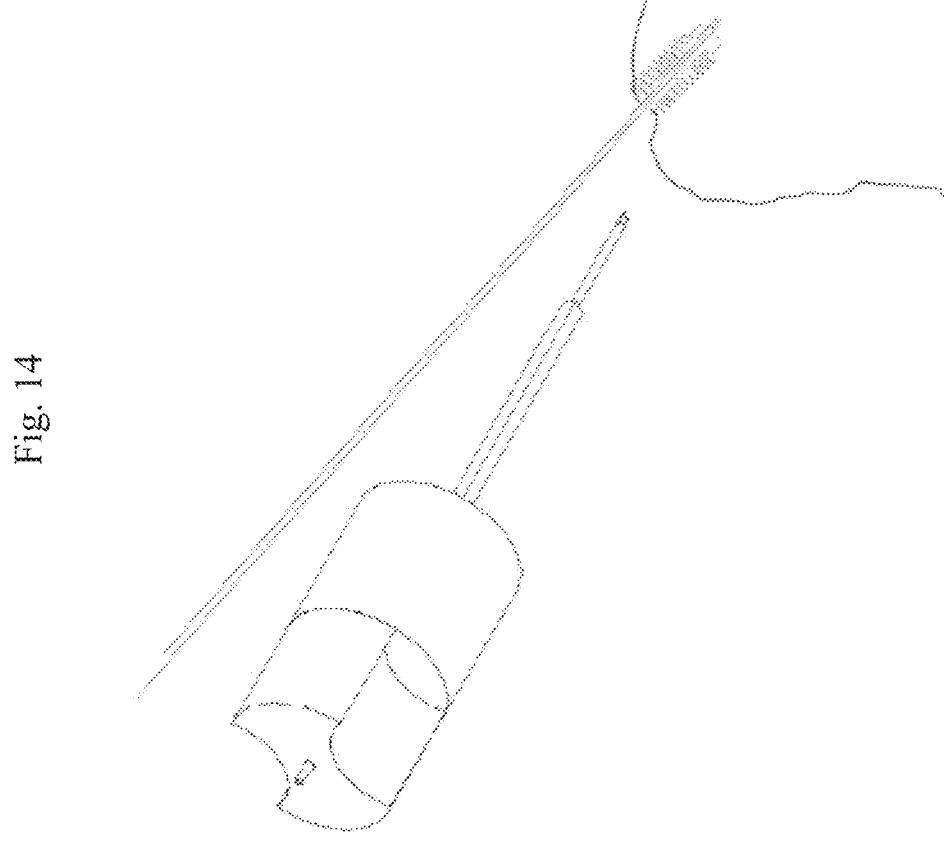
FIG. 14 shows step 1008 of the exemplary method shown in FIG. 10.
Figure 15:
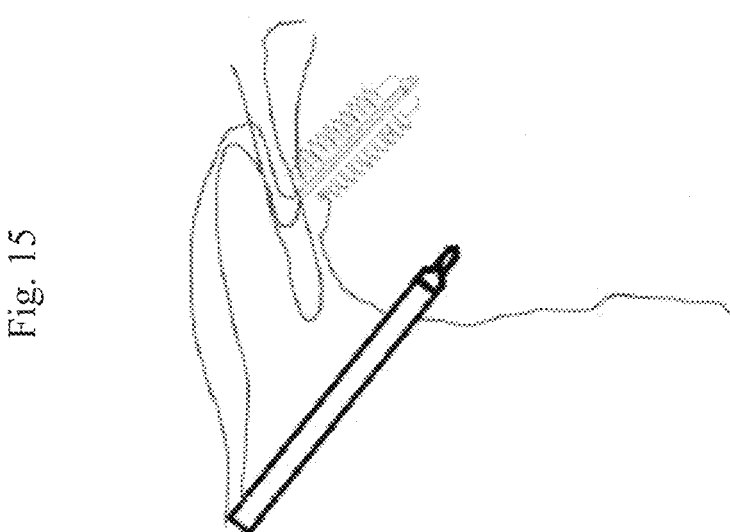
FIG. 15 shows step 1010 of the exemplary method shown in FIG. 10.
Figure 16:
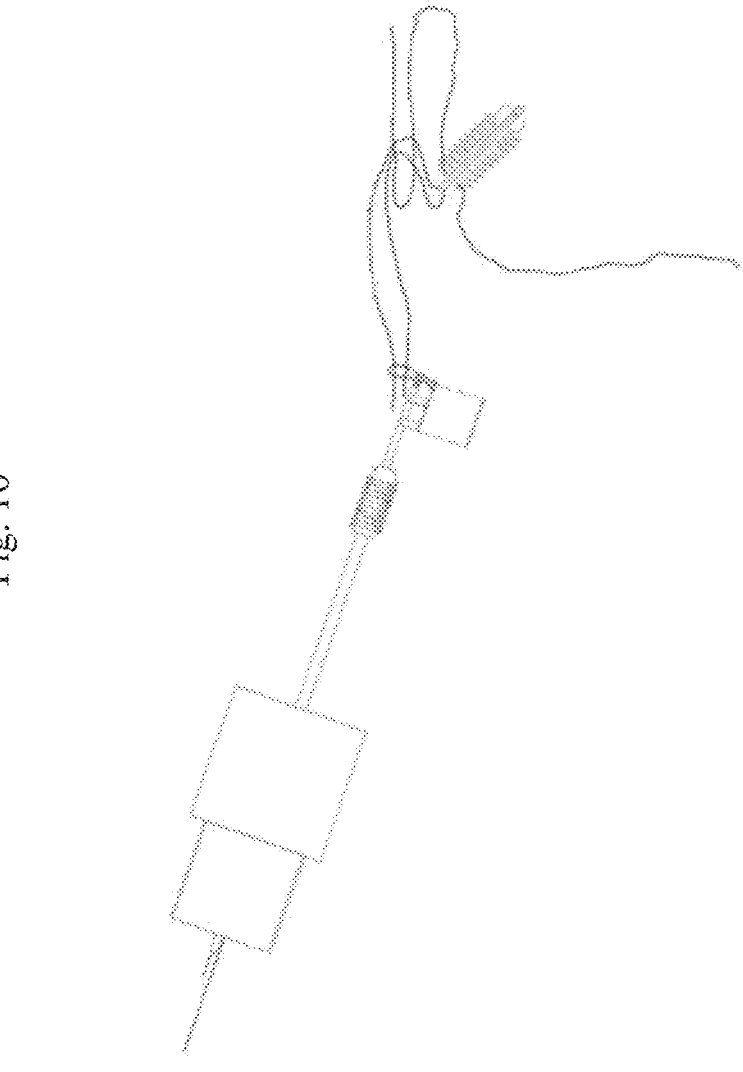
FIG. 16 shows step 1012 of the exemplary method shown in FIG. 10.
Figure 17:
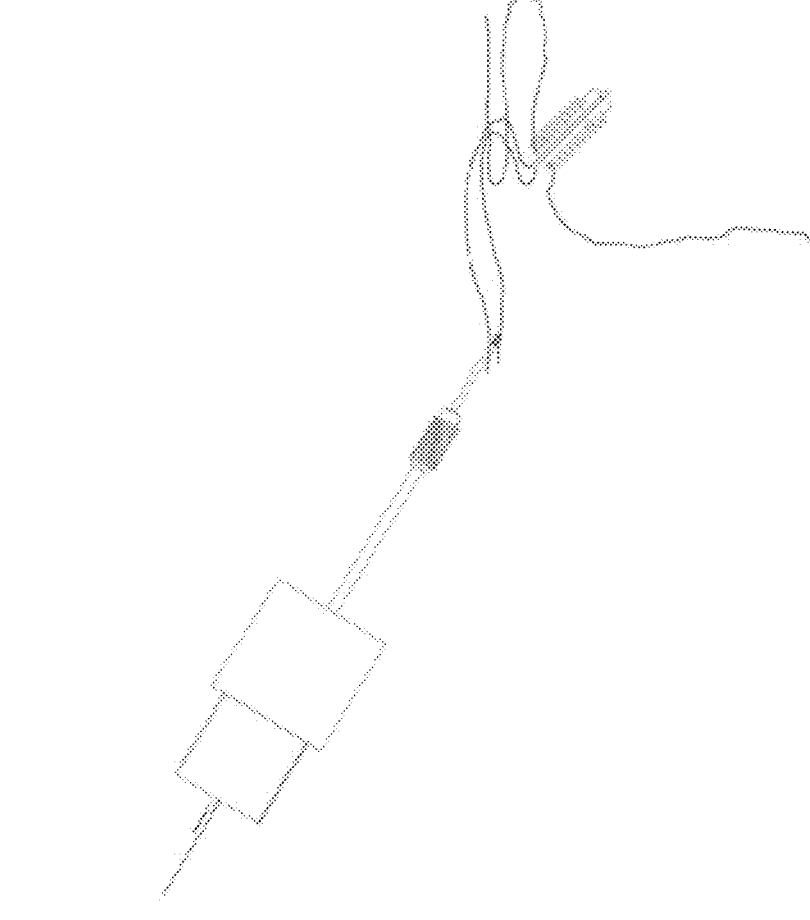
FIG. 17 shows step 1014 of the exemplary method shown in FIG. 10.
Figure 18:
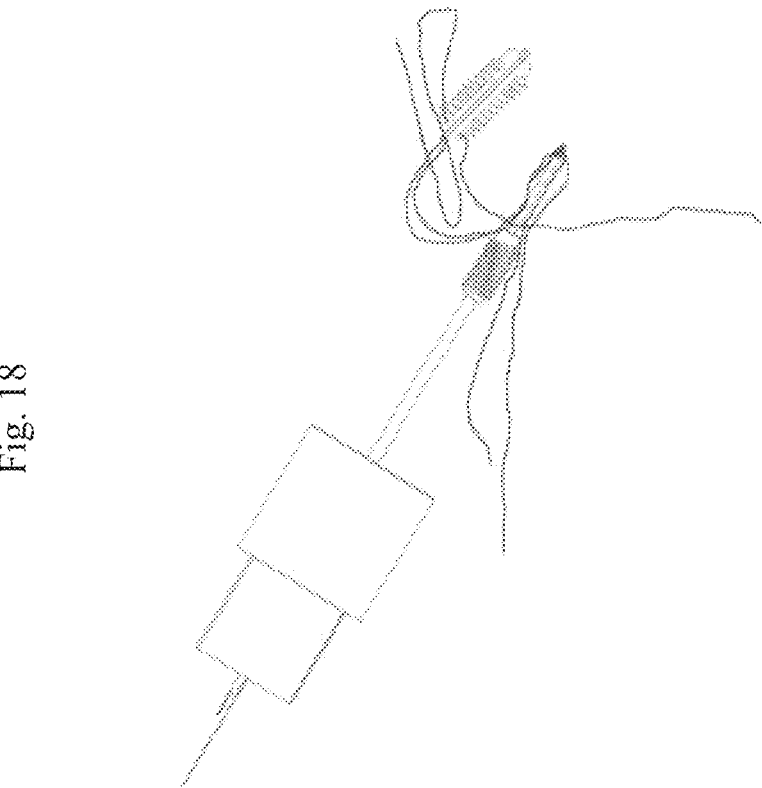
FIG. 18 shows step 1016 of the exemplary method shown in FIG. 10.
Figure 19:
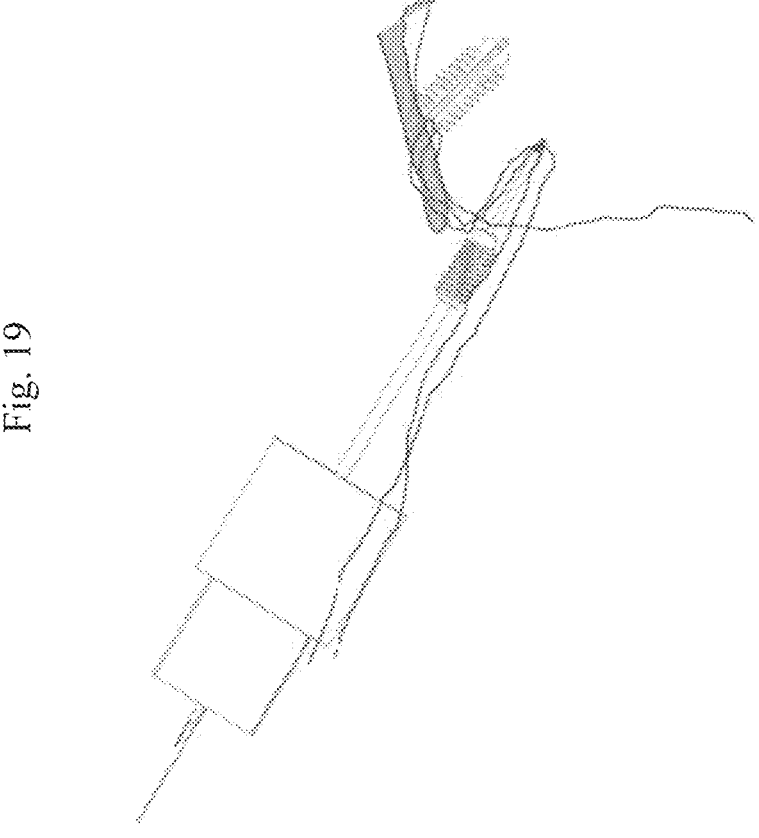
FIG. 19 shows step 1020 of the exemplary method shown in FIG. 10.
Figure 20:
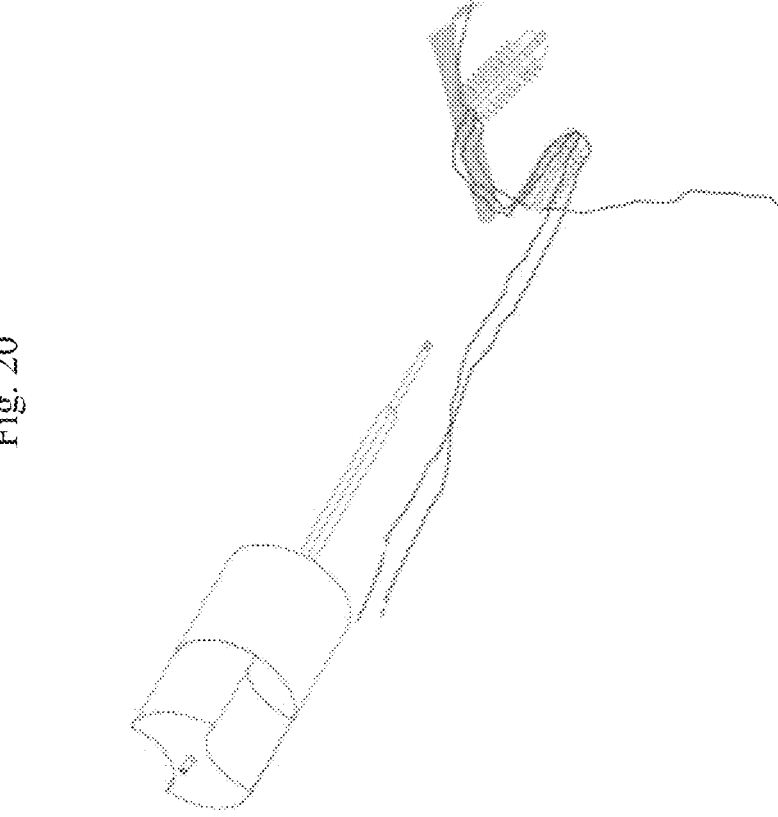
FIG. 20 shows step 1022 of the exemplary method shown in FIG. 10.

Referring generally to FIGS. 11-20, FIGS. 11-20 are exemplary illustrations that describe the exemplary method of FIG. 10. FIG. 11 may correspond to step 1002, FIG. 12 may correspond to step 1004, FIG. 13 may correspond to step 1006, FIG. 14 may correspond to step 1008, FIG. 15 may correspond to step 1010, FIG. 16 may correspond to step 1012, FIG. 17 may correspond to step 1014, FIG. 18 may correspond to step 1016, FIG. 19 may correspond to step 1020, and FIG. 20 may correspond to step 1022.

Figure 21:
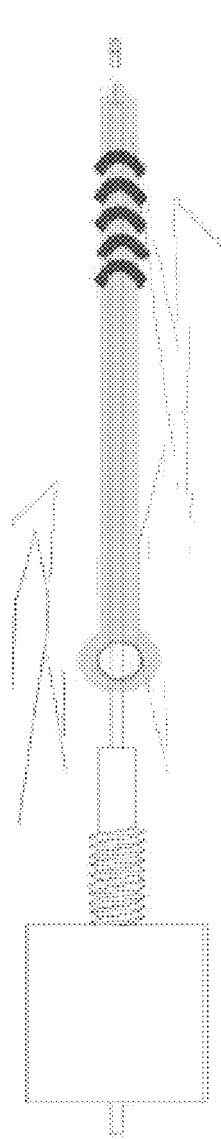
FIG. 21 shows an alternative embodiment for using the suture sleeve.

Exemplary FIG. 21 shows an alternative embodiment for using the suture sleeve. A metal screw with a rounded end may be inserted into plates or bone. The sleeve may sit at the end of the metal screw and act as a receptacle and may allow for the sutures to come out of the screw head to be used as a tension band, or be used for other suture repair of cartilage, bone, or tissue.

Figure 22:
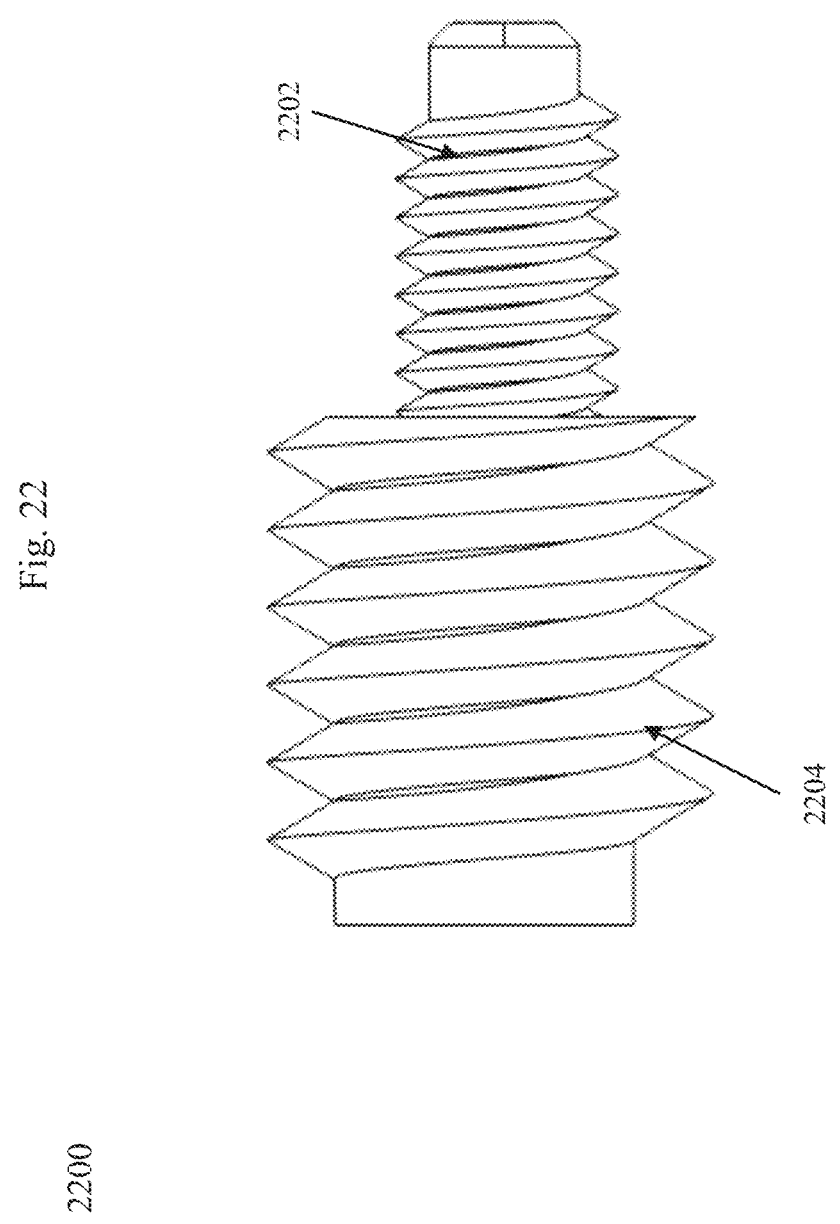

Exemplary FIG. 22 shows an exemplary double diameter screw 2200. The double diameter screw 2200 may have a first smaller diameter 2202 screw section and a second larger diameter 2204 screw section.

Figure 23:
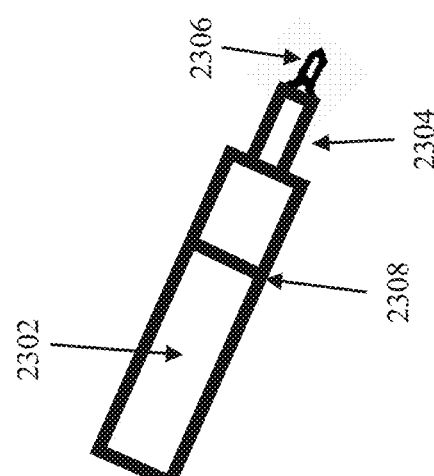
FIG. 23 shows an exemplary triple diameter drill bit.

Exemplary FIG. 23 shows an exemplary triple diameter drill bit 2300. The triple diameter drill 2300 may have a first large diameter 2302 drill portion and a second smaller diameter 2304 which may make a hole for a distal screw tip. The triple diameter drill bit 2300 may further have a tip 2306, which may make a hollow for a suture sleeve. It may be understood that the drill may be used only up to a predetermined drill limit 2308.

Figure 24:
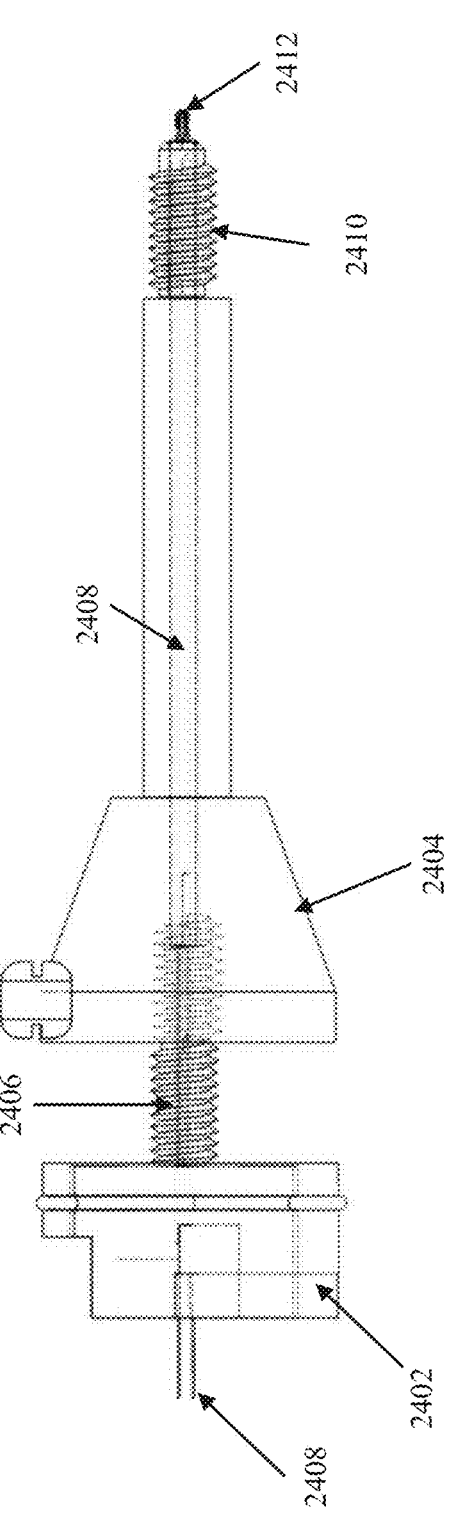
FIG. 24 shows an exemplary flipped handle and driver.

Exemplary FIG. 24 shows a flipped handle and driver 2400, which may be an alternative driver tool for driving the screw and suture sleeve during implantation. The flipped handle and driver 2400 may have a turning driver 2402 a sleeve pusher 2404. It may be understood that when the sleeve pusher 2404 is held and the turning driver 2402 is turned the sleeve pusher 2404 may advance through driver threading 2406. Interior the sleeve pusher 2404 there may be a screw insertion tube 2408 which may hold the sutures traveling from the screw. A screw 2410 may be held at the end of the flipped handle and driver, with a suture sleeve 2412 attached at the tip.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An expandable surgical sleeve, comprising:
   a cylindrical sleeve with a first end opening and a second end opening;
   two holes in the cylindrical sleeve;
   one or more core sutures passed through the first end opening and the second end opening of the cylindrical sleeve;
   a locking suture passed through the two holes in the cylindrical sleeve, wherein at least a portion of the locking suture forms a locking loop outside of the cylindrical sleeve; and
   an extra-sleeve suture configured to pass through tissue and/or bone, and pass through the locking loop; wherein,
   when the one or more core sutures are tensioned, the cylindrical sleeve is configured to engage with surrounding tissue; and
   when the locking suture is tensioned, the expandable surgical sleeve is locked, and the extra-sleeve suture is locked at a constant tension.

2. The expandable surgical sleeve of claim 1, wherein the cylindrical sleeve is comprised of at least polyester and/or polyethylene.

3. The expandable surgical sleeve of claim 1, wherein the two holes in the cylindrical sleeve are on opposite sides of the cylindrical sleeve.

4. The expandable surgical sleeve of claim 1, wherein the two holes are staggered on the same side of the surgical sleeve.

5. The expandable surgical sleeve of claim 1, wherein the one or more core sutures are tied to the locking suture.

* * * * *